United States Patent [19]
Matthiessen

[11] Patent Number: 4,833,909
[45] Date of Patent: May 30, 1989

[54] GAS-SENSING APPARATUS

[75] Inventor: Hans Matthiessen, Gross Parin, Fed. Rep. of Germany

[73] Assignee: Drägerwerk Aktiengesellschaft, Lübeck, Fed. Rep. of Germany

[21] Appl. No.: 142,523

[22] Filed: Jan. 11, 1988

[30] Foreign Application Priority Data

Jan. 9, 1987 [DE] Fed. Rep. of Germany ....... 3700460

[51] Int. Cl.$^4$ ............................................. G01N 31/00
[52] U.S. Cl. ....................................................... 73/23
[58] Field of Search ................... 73/23, 27 R; 422/83, 422/98; 204/1 T; 340/632

[56] References Cited

U.S. PATENT DOCUMENTS

| | | | |
|---|---|---|---|
| 3,673,853 | 7/1972 | Griswold et al. | 73/19 |
| 3,854,320 | 12/1974 | Burroughs et al. | 73/23 |
| 4,384,925 | 5/1983 | Stetter et al. | 204/1 T |
| 4,627,269 | 12/1986 | Forster et al. | 73/23 |

Primary Examiner—Hezron E. Williams
Attorney, Agent, or Firm—Walter Ottesen

[57] ABSTRACT

The invention is directed to an apparatus for sensing a gaseous component in air and includes a housing having a flushing chamber through which an air sample can flow via a closeable inlet and a closeable outlet. The sensor is mounted in a measuring chamber above the flushing chamber and is hermetically sealed from its ambient not only during the time that the flushing chamber is flushed with the air sample; rather, and most important, during the measuring operation itself in order that any influences from a diffusion of the ambient air into the measuring chamber is prevented. For this purpose and to determine the sample quantity diffusing into the measuring chamber at the beginning of a specific period of time, the inlet as well as the outlet of the flushing chamber is closed while at the same time the diffusion passage interconnecting the two chambers is opened. After the time period has run, the diffusion passage is again closed.

4 Claims, 1 Drawing Sheet

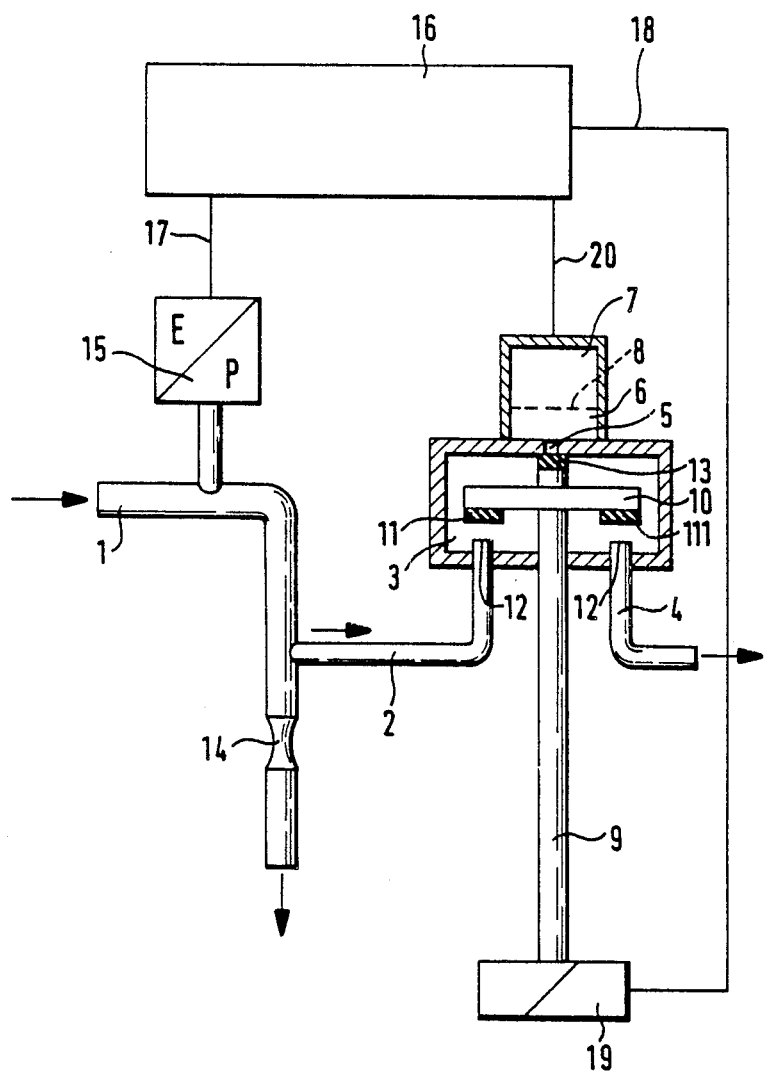

GAS-SENSING APPARATUS

FIELD OF THE INVENTION

The invention relates to an apparatus for sensing a gaseous component in air and includes a sample chamber having a sensor. An air sample can flow through the chamber via a closeable inlet and a closeable outlet.

BACKGROUND OF THE INVENTION

U.S. Pat. No. 4,384,925 discloses a sensing apparatus wherein a sensor housing having a sensor is mounted in a flow line for an air sample to be investigated. From time to time, the flow line is interrupted upstream and downstream of the sensor so that a definite quantity of the air sample is enclosed in this line segment and the sensor housing. The sensor operates pursuant to the coulometric principle so that the measured charge carriers during a time period predetermined by a control unit are a measure for the gas concentration contained in the closed-off air-sample chamber. This value is then utilized as a calibration value for the continuous measurement which follows by means of a second independent sensor.

However, the calibration sensor in the above-mentioned sensing apparatus is continuously subjected to the air sample also before the actual calibration so that when the calibration begins with the closing off of the sensor housing, a non-reproducible gas concentration is present which often changes. These unstable measurement conditions can considerably delay the measurement time until stable conditions are reached. Furthermore, the interrupted segments of the flow line are likewise to be viewed as portions of the measurement chamber wherein voids of the air sample having a concentration other than in the sensor chamber can become trapped and which contribute to falsifying the measuring result.

A further sensing device is disclosed in U.S. Pat. No. 3,854,320. This sensing device includes a sample chamber in which the gas to be investigated is introduced via an inlet and is released to the ambient via an open outlet after the sample chamber has been flushed. In this embodiment, the gas to be investigated is the exhaled breathing gas of a subject person. A sensor is disposed in the interior of the sample chamber and is covered with a shield or cover during the flushing phase. The sensor senses a component of gas contained in the air sample and for the embodiment shown, the gas component is alcohol contained in the breath. If a significant air sample is present in the sample chamber after a sufficiently long flushing duration, the cover over the sensor is lifted so that the latter is freely exposed to the air sample to be investigated in the sample chamber. During this exposure time, the sensor delivers a signal to an evaluation unit which then indicates the concentration of the gas component to be sensed in the sample chamber. The inlet is closed during the measuring time so that no further air sample can flow into the sample chamber. The cover is again placed over the sensor when the measuring step is to be ended so that the sensor is sealed with respect to the sample chamber. At the same time, the sensor and the space enclosed by the sensor cover are flushed with ambient air to remove any residual quantity of the sample gas which is still present in the encapsulated sensor chamber.

In this known sensing device, the sample chamber is separated only from the inlet with respect to flow during the measurement. However, a continuous and significan gas exchange with the ambient atmosphere takes place via the open outlet so that the initial concentration of the gas to be sensed during the measurement continuously reduces because of the external influences.

SUMMARY OF THE INVENTION

In view of the foregoing, it is desirable to improve upon a sensing device of the type described above so that the sensor has a stable initial position uninfluenced by the test gas flow before the beginning of the measuring period. It is a further object of the invention to provide an improved gas-sensing apparatus wherein the sample chamber has the smallest possible volume while at the same time offering a low flow resistance for the air sample to thereby attain a short measuring time.

According to a feature of the sensing apparatus according to the invention, the sample housing is partitioned into a measuring chamber containing the sensor and a flushing chamber with both chambers being interconnected via a closeable measuring chamber opening. Pursuant to a further feature of the sensing apparatus, the inlet as well as the outlet open into the flushing chamber. To establish the quantity of the sample diffused into the measuring chamber at the beginning of a specific period of time, the inlet as well as the outlet are closed while at the same time the measuring chamber opening is opened and, after this predetermined period of time has elapsed, the measuring chamber opening is closed.

With the invention, the situation is obtained that stable initial values are provided for the sensor at the beginning of the measuring period because the sensor is covered with respect to the air sample which flows through the flushing chamber before the sample is taken.

A covered sensor operating by consuming the gas component to be detected would then itself return to its zero point as an initial value.

Furthermore, a covered sensor does not falsify the later measuring result by premature consumption of the gas components to be sensed during the time that the sample is taken.

A definable quantity of sample air is provided from the flushing chamber to the sensor in its measuring chamber. This quantity of sample air is determined by setting the size of the measuring chamber. A small measuring chamber volume then results in a correspondingly short measuring time. A sufficiently small flow resistance of the flushing chamber volume can nonetheless be retained so that, for example, the taking of a sample into the flushing chamber by exhalation of a person is possible. The sample quantity trapped in this manner can be subjected to a quantitative analysis without disturbing external influences from the flushing chamber. This can be carried out especially by utilizing electro-chemical sensors by means of a very precise coulometric measurement. Disturbances of the measuring operation through possible thinning of the air sample in the measuring chamber are prevented.

If the measuring chamber opening is configured as a diffusion length, the concentration of the gas compoent to be sensed present in the measuring chamber can be influenced by the length of time that the diffusion length is open when this opening duration is set to be less than the time for the adjustment of a balance between the concentrations in the flushing chamber and the measuring chamber.

For carrying out a measurement at very high concentrations which would drive the sensor into saturation, the concentration can be considerably reduced in this manner by utilizing experimentally determinable correction factors so that an analytical quantitative measurement remains possible.

For the case of a coulometric measurement, only a small component quantity of the air sample available in the flushing chamber is applied for making the measurement. This component quantity is consumed in a considerably shorter time than would be the case for the total quantity.

An especially advantageous embodiment of the sensing apparatus according to the invention includes means for opening the inlet as well as the outlet after the time period has run. This affords the special advantage that during the measuring operation, the flushing chamber can be either flushed with fresh air or a new sample can already be taken.

It is preferable to configure the flushing chamber from a housing wherein the inlet and the outlet as well as the diffusion section all open into the flushing chamber with the ports of inlet and outlet being closeable by means of an inlet seal and an outlet seal mounted on a common seal carrier which, in turn, is mounted on a rod projecting into the flushing chamber. The rod is displaceable in the axial direction by a positioning member. The seal carrier includes a diffusion-length closure means mounted thereon so that the diffusion length is closed when the inlet and outlet ports are open and so that this diffusion length is open when the inlet and outlet ports are closed. In this way, the flushing chamber can be closed with respect to the through-flowing air sample and at the same time the diffusion length can be opened to the measuring chamber with a valve stroke. When the diffusion length is again closed, the inlet and the outlet ports are again opened to the flushing chamber.

BRIEF DESCRIPTION OF THE DRAWING

The invention will now be explained with reference to the single figure of the drawing which shows a preferred embodiment of the gas-sensing apparatus according to the invention.

DESCRIPTION OF THE PREFERRED EMBODIMENTS OF THE INVENTION

Referring to the drawing, the air sample to be investigated is pumped through the test-air line 1 in the direction indicated by the arrow. The test-air line 1 is first connected in the main stream via a throttle 14 with the ambient. From this test-air line 1, a narrower inlet line 2 branches off into the flushing chamber 3 which, in turn, is connected with the ambient via an outlet line 4. The flushing chamber 3 has a diffusion length 5 which defines the connection to the measuring chamber 6 for a sensing sensor 7. The sensor 7 is partitioned off from the measuring chamber 6 by means of a separating element 8 which is the diffusion membrane for the sensor in the case where the sensor is an electro-chemical sensor. A valve rod 9 projects into the flushing chamber 3 and has a seal carrier 10 mounted at its one end in the flushing chamber 3.

The seal carrier 10 is mounted on the end face of the rod 9 and has rubber-elastic pressure pieces (11, 111) at both its ends which face toward the respective openings 12 of the inlet 2 and the outlet 4. The carrier 10 includes a closure piece 13 which is formed thereon in the form of an extension of the rod 9 and closes the diffusion length 5.

For carrying out a measurement of an air sample, the air sample is first conducted through the test-air line 1 as indicated in the drawing and the greatest portion of this air sample flows off into the ambient. A pressure is developed in the line 1 by the throttle 14 and this pressure is transmitted via pressure-measurement line 17 to a control unit 16 by means of a pressure sensor 15. A component flow of the air sample is conducted into the flushing chamber 3 via the open inlet 2. This component flow divides in the flushing chamber 3 and is discharged to the ambient through open outlet 4.

Insofar as a specific pressure was present at the pressure sensor 15 for a time predetermined by the control unit 16, the valve rod 9 is displaced into a position in which the openings 12 of the inlet 2 and of the outlet 4 are simultaneously closed by the respective pressure pieces (11, 111). The valve 19 is controlled by the control unit 16 via the valve-control line 18. At the same time, the diffusion section 5 is opened because the closure piece 13 is moved away therefrom and the air sample located in the flushing chamber 3 can diffuse through the diffusion length 5 into the measuring chamber 6.

The sensing sensor 7 is activated for a measurement by the control unit 16 via the sensor line 20. After a time period predetermined by the control unit 16 has run, the valve 19 is actuated and the valve rod is again returned to the position shown in the drawing. With this operation, a determinable air-sample quantity has entered the measuring chamber 6. The air-sample quantity is determined by means of the opening time of the diffusion length 5 and now is available for evaluation undisturbed from any kind of influence in the sample-receiving system. By using a coulometric measurement, the gas to be sensed is distorted by the sensing sensor 7 so that the measured current flowing through the electro-chemical sensor 7 can be evaluated by the control unit 16 and displayed as concentration data.

It is understood that the foregoing description is that of the preferred embodiments of the invention and that various changes and modifications may be made thereto without departing from the spirit and scope of the invention as defined in the appended claims.

What is claimed is:

1. An apparatus for sensing a gaseous component in air, the apparatus comprising:
    a housing having an interior space;
    a sensor for sensing the gaseous component;
    partition means for partitioning the interior space of said housing into a flushing chamber and into a measuring chamber for accommodating said sensor therein;
    passage means interconnecting said chambers;
    an inlet line having an opening in said flushing chamber for conducting the air to be tested into said flushing chamber;
    an outlet line having an opening for receiving air in said flushing chamber and conducting the same to the ambient;
    first and second closure means for opening and closing respective ones of the openings of said inlet line and said outlet line in said flushing chamber;
    third closure means for closing and opening said passage means;

actuating means for actuating said first closure means and said second closure means for closing the opening of said inlet line and the opening of said outlet line and for actuating said third closure means for opening said passage means simultaneously with the closure of the respective openings of said inlet and outlet lines; and, a control unit connected to said actuating means for energizing said actuating means to permit a sample quantity of the gaseous component to diffuse into the measuring chamber from said flushing chamber when said third closure means is open at the beginning of a predeterminable time period and for again actuating said actuating means to cause said third closure means to reclose said passage means after said time period has expired.

2. The apparatus of claim 1, said partition means being a partition wall extending across said housing for partitioning the same into said flushing chamber and said measuring chamber; and, said passage means being formed as a passage through said partition wall for interconnecting said chambers; and, said passage being configured to define a diffusion length.

3. The apparatus of claim 1, said control unit being connected to said actuating means for energizing said actuating means to also open said openings of aaid inlet line and said outlet line in said flushing chamber after said time period has run.

4. The apparatus of claim 2, said actuating means comprising a movable rod extending with one of its ends into said flushing chamber; a carrier mounted on said one end so as to be movable with said rod in said flushing chamber when the latter is moved; said first and second closure means being respective first and second seals both mounted on said carrier directly adjacent respective ones of said openings of said inlet and outlet lines for closing and opening said openings of said lines in response to an axial movement of said rod; said third closure means being an additional seal disposed directly adjacent said passage means; and, said seals being arranged on said carrier so as to cause said additional seal to be in closing contact with said passage while at the same time said first and second seals are displaced from said openings.

* * * * *

UNITED STATES PATENT AND TRADEMARK OFFICE
CERTIFICATE OF CORRECTION

PATENT NO. : 4,833,909

DATED : May 30, 1989

INVENTOR(S) : Hans Matthiessen

It is certified that error appears in the above-identified patent and that said Letters Patent is hereby corrected as shown below:

In column 2, line 2: delete "nifican" and substitute -- nificant -- therefor.

In column 6, line 5: delete "aaid" and substitute -- said -- therefor.

Signed and Sealed this

Twentieth Day of February, 1990

*Attest:*

JEFFREY M. SAMUELS

*Attesting Officer*   *Acting Commissioner of Patents and Trademarks*